(12) United States Patent
Ortenzi et al.

(10) Patent No.: US 12,364,666 B2
(45) Date of Patent: Jul. 22, 2025

(54) STABLE LOW DIGESTIVE ENZYME CONTENT FORMULATION

(71) Applicant: SOCIÉTÉ DES PRODUITS NESTLÉ S.A., Vevey (CH)

(72) Inventors: Giovanni Ortenzi, Monza (IT); Giuseppe De Franza, Milan (IT); Danilo Clementi, Seriate (IT); Christian Stollberg, Carugate (IT); Luigi Boltri, Agrate Brianza (IT)

(73) Assignee: Societe des Produits Nestle S.A., Vevey (CH)

( * ) Notice: Subject to any disclaimer, the term of this patent is extended or adjusted under 35 U.S.C. 154(b) by 630 days.

(21) Appl. No.: 17/750,648

(22) Filed: May 23, 2022

(65) Prior Publication Data
US 2022/0280433 A1     Sep. 8, 2022

Related U.S. Application Data

(62) Division of application No. 13/251,926, filed on Oct. 3, 2011, now Pat. No. 11,364,205.

(60) Provisional application No. 61/389,037, filed on Oct. 1, 2010.

(51) Int. Cl.
| | |
|---|---|
| *A61K 9/20* | (2006.01) |
| *A61K 9/28* | (2006.01) |
| *A61K 9/48* | (2006.01) |
| *A61K 38/46* | (2006.01) |

(52) U.S. Cl.
CPC .......... *A61K 9/2054* (2013.01); *A61K 9/2072* (2013.01); *A61K 9/2866* (2013.01); *A61K 9/4808* (2013.01); *A61K 38/465* (2013.01)

(58) Field of Classification Search
CPC ...... A61K 9/25; A61K 9/2054; A61K 9/2866; A61K 9/4808
See application file for complete search history.

(56) References Cited

U.S. PATENT DOCUMENTS

2011/0064799 A1*   3/2011   Perrett ................. A61K 38/465
                                                  424/490

OTHER PUBLICATIONS

Avicel fact sheet (Avicel for Solid Dose Forms, FMC biopolymer (Year: 2010).*

\* cited by examiner

*Primary Examiner* — Micah Paul Young
(74) *Attorney, Agent, or Firm* — K&L Gates LLP (57) ABSTRACT

The present invention is directed to a pharmaceutical composition or dosage form having a stable, low (diluted) digestive enzyme content comprising at least one digestive enzyme and at least one carrier, or a dosage form thereof. The invention is also directed to a process of preparation of the composition or the dosage form. In addition the invention is directed to the treatment and prevention of disorders or conditions associated with a digestive enzyme deficiency in a patient in need thereof, comprising administering to said patient a pharmaceutically acceptable amount of the composition having a stable low digestive enzyme content or dosage form thereof.

23 Claims, 1 Drawing Sheet

STABLE LOW DIGESTIVE ENZYME CONTENT FORMULATION

CROSS-REFERENCE TO RELATED APPLICATIONS

This application is a divisional of U.S. patent application Ser. No. 13/251,926 filed Oct. 3, 2011, which claims priority to U.S. Provisional Application Ser. No. 61/389,037, filed Oct. 1, 2010, each of which is herein incorporated by reference in its entirety.

FIELD OF THE INVENTION

In various embodiments, the present invention is directed to pharmaceutical compositions having a stable, low (diluted) digestive enzyme content comprising at least one digestive enzyme and at least one carrier, or a dosage form thereof. In other embodiments, the invention is also directed to processes of preparation of the composition or the dosage form. In additional embodiments, the invention is directed to the treatment and prevention of disorders associated with a digestive enzyme deficiency in a patient in need thereof, comprising administering to said patient a pharmaceutically acceptable amount of the composition having a stable low digestive enzyme content or dosage form thereof.

BACKGROUND OF THE INVENTION

The proper dosing of medications for patients is an important concern within the medical field. For infants or smaller children, or geriatric patients in particular, and sometimes also for adult populations, the administration of medications and dosing methods often present substantial issues. As is well known in the art, medications are provided in many forms (e.g., liquid, solid, and combinations of solids in liquids) and are delivered to patients in many way (e.g., orally, via injection, transdermally).

The FDA estimates that more than 200,000 Americans suffer from exocrine pancreatic insufficiency (EPI). EPI involves a physiological disorder wherein individuals are incapable of properly digesting food due to a lack of digestive enzymes made by their pancreas. That lack of digestive enzymes leads to disorders such as the maldigestion and malabsorption of nutrients, which lead to malnutrition and other consequent undesirable physiological conditions associated therewith. These disorders are common for those suffering from cystic fibrosis (CG) and other conditions compromising the exocrine function of the pancreas, such as pancreatic cancer, pancreatectomy, and pancreatitis. The malnutrition can be life threatening if left untreated, particularly in the case of infants and CF patients, and the disorders can lead to impaired growth, compromised immune response, and shortened life expectancy.

Digestive enzymes, such as pancrelipase and other pancreatic enzymes products (PEPs), can be administered to at least partially remedy EPI. The administered digestive enzymes provide for patients to be able to more effectively digest their food. Enzyme therapy is a critical aspect of clinical management of nutrition and digestion in the CF population. Recently published infant guidelines recommend immediate initiation of PERT (pancreatic Enzyme Replacement Therapy) in CF newborns with symptomatic or confirmed pancreatic insufficiency. Within this framework an optimal dosing regimen has to be identified. It is believed that the use of PERT in infants may improve short and long term growth and nutritional outcomes, and subsequently increase lung function and ultimately survival.

Pancreatic enzymes, which have been used in the treatment of EPI to compensate for lost of digestive function, have been in use for more than 60 years. Their use until recently was not subject modern regulatory guidelines governing drug approvals based on safety, and efficacy, and manufacturing controls. Recently, pancreatic enzyme replacement therapies have become the subject of US and European regulatory authority initiatives that require that marketed pancreatic enzyme products go through the current drug approval process in order to remain in commerce. Zenpep®, Creon® and Pancreaze® are three products that successfully went through the process set by the FDA and are approved for marketing in the United States. In other territories/countries where similar initiatives are still proceeding or have not been implemented as yet, a variety of pancreatic enzyme products are still available.

Capsules containing digestive enzymes such as pancrelipase have been developed for oral administration. However, if a patient is unable to swallow the capsules, each capsule can be opened and the contents sprinkled on a small amount of food, usually a soft, acidic food (such as commercially available applesauce) and administered orally to the patient with a spoon. Alternatively, such medications may be administered orally for infants and children, using a syringe device containing the contents suspended in a medium amenable to administration thereby.

The pancrelipase products are generally labeled as containing three enzyme classes: lipase, amylase, and protease, and the levels or potency of which are listed. These enzymes catalyze the hydrolysis of fats into glycerol and fatty acids, starch into dextrin and sugars, and proteins into amino acids and derived substances. Digestion is, however, a complex process involving many other enzymes and substrates that contribute to correct digestive functioning and producing the full range of digestive products. Other enzymes contained in pancrelipase include trypsin, carboxypeptidases, elastases, phospholipases, and cholesterases amongst other and various co-factors and coenzymes. These substances are produced naturally in the pancreas and also contribute to correct digestive functioning.

Pancrelipase is typically prepared from porcine pancreatic glands, although other sources can also be used, for example those described in U.S. Pat. No. 6,051,220, U.S. 2004/0057944, 2001/0046493, and WO 2006044529, each of which is herein incorporated by reference in its entirety for all purposes.

Pancreatic enzymes show optimal activity under near neutral and slightly alkaline conditions. Under gastric conditions, pancreatic enzymes may be inactivated with a resulting loss in biological activity. Therefore, exogenously administered enzymes are generally protected against gastric inactivation and remain intact during their transit through the stomach and into the duodenum. Therefore it is desirable to coat pancreatic enzymes. Pancreatic lipases are the most sensitive to gastric inactivation and are the most important class of enzymes in the treatment of malabsorption. Lipase activity is typically monitored to determine the stability of an enzyme composition containing lipase.

The entire contents of U.S. Pat. No. 7,658,918 issued to Ortenzi et al. is expressly incorporated by reference in its entirety herein for all purposes. U.S. Pat. No. 7,658,918 describes stable digestive enzymes compositions and explains that certain particulate medications, administered orally, are designed to pass through the stomach of the patient and thereafter to release within the intestines; the total amount of pancrelipase (by weight) in the cores of the particles comprised in the compositions or oral dosage forms disclosed in said patent is 68-90%.

Aptalis Pharma markets at least some multiparticulate enterically coated pancrelipase enzymes beads medications. For example, Aptalis Pharma markets delayed-release capsules for the treatment of exocrine pancreatic insufficiency (EPI) in patients under the designation EUR-1008 and the registered trademark Zenpep®. Each Zenpep® capsule for oral administration contains enteric coated beads with high pancrelipase content (1.8-1.9 mm for 3,000, 5,000 USP units of lipase, 2.2-2.5 mm for 10,000, 15,000 and 20,000 and 25,000 USP units of lipase).

All of the marketed pancrelipase products have very high pancrelipase content.

Some commercially available digestive enzyme compositions show a loss of lipase activity over time of up to about 35% or more. In order to compensate for the loss of enzymatic activity during storage and to ensure that the product provides the label-claimed potency at the end of the shelf life, manufacturers typically overfill the dosage forms from 5% to 60% and current USP specifications for Pancrelipase Delayed-Release Capsules allow for Pancrelipase equivalent to not less than 90% and not more than 165% of the labeled lipase activity, in practice this means that patients and prescribers are sometimes unable to judge the dosage strength with accuracy, with the practical result that the appropriate dosage needs to be determined empirically for each new prescription. Patients with exocrine pancreatic insufficiency disorders rely on these drugs to provide the enzymes they need to digest food properly. If the label contains an inaccurate statement about a particular product's potency, then the patient is at risk for receiving too much or too little of the medicine.

In addition, there exist several situations in which a low dosage is needed and proper dosing of the medication cannot be achieved using the existing high dosage formulations. This becomes particularly relevant when pancrelipase should be a administered in infants with a dose ranging from 500 units lipase per meal per kg body weight to 2,000 units lipase per meal per kg then, low dosage or diluted pancrelipase dosage form should be available for administration.

It is generally known that the preparation of low dosage forms having a uniform drug content faces several problems. In addition to that, in case of pancrelipase, both the composition and the process of preparation of a final diluted formulation should be as such as to ensure the proper stability upon storage of the labile enzymes.

Accordingly, it would be desirable to provide a stable low dosage or diluted digestive enzymes composition having high content uniformity and capable of maintaining the necessary activity for the expected shelf life of the enzymes preparation.

BRIEF SUMMARY OF THE INVENTION

To achieve these and other objects, and to meet these and other needs, and in view of its purposes, the present invention relates to a stable low dosage digestive enzyme composition, and dosage form comprised thereof.

More particularly, in various embodiments, the present invention relates to a stable, highly diluted enzyme composition and dosage form that comprise a plurality of digestive enzymes beads, more particularly enterically coated beads. The diluted digestive enzyme beads have high content uniformity and exhibit minimal loss of enzymatic activity upon storage.

The present invention provides for a suitable package comprising a sealed container made of moisture resistant material, a desiccant, and at least one dosage form according to the invention.

Moreover, the present invention provides a method of preparing the stable, low dosage digestive enzyme composition and dosage form thereof. The method comprises preparing, a suitable diluted digestive enzyme blend with at least one carrier to ensure the high uniformity in digestive enzyme content, and then coating the heads with a solution comprising an enteric polymer, thereby forming a plurality of stable enterically coated diluted digestive enzyme-containing beads.

DETAILED DESCRIPTION OF THE INVENTION

The present invention is directed to a stable composition comprising at least one digestive enzyme, and at least one carrier wherein:
  a) the total amount of digestive enzymes in the composition is from about 4 to about 20% by weight; or
  b) at least one carrier of the composition has a large particle size; or
  c) the total amount of digestive enzymes in the composition is from about 4 to about 20% by weight, and at least one carrier of the composition has a large particle size.

In another embodiment, the total amount of the digestive enzymes in the composition ranges from about 5 to about 19% by weight.

In another embodiment, the total amount of the digestive enzymes in the composition ranges from about 10 to about 15% by weight. In another embodiment of the invention, the total amount of the digestive enzymes in the composition ranges from about 4%, or about 5%, or about 10%, or about 15%, or about 19% by weight, inclusive of all ranges and sub-ranges there between.

In the composition of the invention, the digestive enzymes are in form of beads, preferably in the form of enterically coated pancrelipase beads.

In various embodiments of the invention, the diluted digestive enzymes beads comprise: from about 4 to about 20 wt. % of pancrelipase and from about 70 to about 96% of at least one carrier; or from about 5 to about 19 wt. % pancrelipase and from about 71 to about 95% of at least one carrier, or from about 10 to about 15 wt. % of pancrelipase and from about 75 to about 90% of at least one carrier, wherein each said wt. % is based on the total weight of the uncoated beads.

In one further embodiment of the invention, the beads that are enterically coated comprise; from about 10 to about 15 wt. % of pancrelipase and from about 80 to about 85% of at least one carrier, wherein each said wt. % is based on the total weight of the uncoated beads.

In the present invention, low pancrelipase content powder blends are disclosed that e high content uniformity and very low segregation while also showing excellent flowability. These blends are particularly suitable for producing the low or diluted pancrelipase beads.

For the present invention, the digestive enzyme beads include any kind of particulate. The term "bead" includes granules, tablets, spheres, minitablets, microtablets, microparticles, microspheres, minimicrospheres, microcapsules, micropellets, as well as particles up to about 5 mm in diameter. The bead may be any suitable particle size or shape. For example, the beads can have a particle size range of about 50 μm to about 5,000 μm, or of about 50 μm to about 2,000 μm, they can have a nominal (e.g., mean) particle diameter in the range of about 2 to about 5 mm, or of less than about 2 mm for example of about 0.5 to about 2 mm. Beads may have diameters for example of about 0.7 to about 1.6 mm, or of about 0.7 to about 1.25 mm, or of about 0.7 to about 1.25 mm. "Minimicrospheres" having the smallest median particle size of about 1.15 mm or "microtablets" having highest median particle size at about 2.63 mm are also suitable for the present process. The beads can have an average particle size of less than about 800 μm preferably less than about 500 μm, preferably of about 400 μm to about 600 μm or of about 250 μm to about 500 μm. These beads may have a volume diameter (d(v,0.1) (defined as the diameter where 10% of the volume distribution is below this value and 90% is above this value) of not less than 400 μm and a volume diameter d(v,0.9) (defined as the diameter where 90% of the volume distribution is below this value and 10% is above this value) of not more than 900 μm.

All these diluted digestive enzymes beads, more particularly pancrelipase enzymes beads, suitable for the preparation of pharmaceutical products may be enterically coated beads. In embodiments where there is an enteric coating, this coating acts as a barrier, protecting the drug substance from the acidic environment of the stomach and substantially prevents the release of the medication before it reaches the small intestine (i.e., the release of enzyme in the stomach is less than about 10 to about 20% of the total amount of enzyme in the composition). Suitable combinations of enteric coating compositions with other coating compositions can be used to provide the desired type of control over drug release or therapeutic effects. The enteric coating includes at least one enteric polymer and further excipients. The phrase "enteric polymer" means a polymer that protects the digestive enzymes from gastric contents, for example a polymer that is stable at acidic pH, but can break down rapidly at higher pH or a polymer whose rate of hydration or erosion is slow enough to ensure that contact of gastric contents with the digestive enzymes is relatively minor while it is in the stomach, as opposed to the remainder of the gastro-intestinal tract.

The compositions and dosages forms of the invention comprise at least one digestive enzyme.

The term "digestive enzyme" used herein denotes an enzyme in the alimentary tract which breaks down the components of food so that they can be taken or absorbed by the organism. Non-limiting examples of digestive enzymes include pancrelipase (also referred to as pancreatin), lipase, co-lipase, trypsin, chymotrypsin, chymotrypsin B, pancreatopeptidase, carboxypeptidase A, carboxypeptidase, B, glycerol ester hydrolase, phospholipase, sterol ester hydrolase, elastase, kininogenase, ribonuclease, deoxyribonuclease, α-amylase, papain, chymopapain, glutenase, bromelain, ficin, β-amylase, cellulase, β-galactosidase, isomaltase, and mixtures thereof. They are obtained through extraction from the pancreas or pancreatic juices or produced artificially or obtained from sources other than pancreas such as from microorganisms, bacteria, mold, fungi, plants or other animal tissues, genetically modified microorganisms, fungi or plants.

The terms "pancrelipase" or "pancrelipase enzymes" or "pancreatin" denotes a mixture of several types of enzymes, including amylase, lipase, and protease enzymes, or mixtures thereof having pancreatic origin. Pancrelipase is commercially available, for example from Nordmark Arzneimittel GmbH, Scientific Protein Laboratories LLC or Sigma Aldrich; and similar extracts from porcine, bovine or other mammalian sources may be used.

The term "lipase" denotes an enzyme that catalyzes the hydrolysis of lipids to glycerol and simple fatty acids. Examples of lipases suitable for the present invention include, but are not limited to animal lipases (e.g., porcine lipases), bacterial lipases (e.g., Pseudomonas lipase and/or Burkholderia lipase), fungal lipases, plant lipases, recombinant lipases (e.g., produced via recombinant DNA technology by a suitable host cell, selected from any one of microorganisms, bacteria, yeast, fungi, plants, insects or mammalian host cells in culture, or recombinant lipases which include an amino acid sequence that is homologous or substantially identical to a naturally occurring sequence, lipases encoded by a nucleic acid that is homologous or substantially identical to a naturally occurring, lipase-encoding nucleic acid, etc.), synthetic lipase, chemically-modified lipase, and mixtures thereof. The term "lipids" broadly includes naturally-occurring molecules including fats, waxes, sterols, fat-soluble vitamins (such as vitamins D, E and K), monoglycerides, diglycerides, triglycerides, phospholipids, etc.

The term "amylase" refers to glycoside hydrolase enzymes that break down starch, for example α-amylases, β-amylases, γ-amylases, acid α-glucosidases, salivary amylases such as ptyalin, etc, Amylases suitable for use in the present invention include, but are not limited to animal amylases, bacterial amylases, fungal amylases (e.g., *Aspergillus* amylase, for example, *Aspergillus oryzae* amylase), plant amylases, recombinant amylases (e.g., produced via recombinant DNA technology by a suitable host cell, selected from any one of microorganisms bacteria, yeast, fungi, plants, insects or mammalian host cells in culture, or recombinant amylases which include an amino acid sequence that is homologous or substantially identical to a naturally occurring sequence, amylases encoded by a nucleic acid that is homologous or substantially identical to a naturally occurring amylase-encoding nucleic acid, etc.), chemically modified amylases, and mixtures thereof.

The term "protease" refers generally to enzymes (e.g., proteinases, peptidases, or proteolytic enzymes) that break peptide bonds between amino acids of proteins. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism, Non-limiting examples of proteases suitable for use in the present invention include serine proteases, threonine proteases, cysteine proteases, aspartic acid proteases (e.g., plasmepsin) metalloproteases and glutamic acid proteases. In addition, proteases suitable for use in the present invention include, hut are not limited to animal proteases, microbial proteases, bacterial proteases, fungal proteases (e.g., an *Aspergillus melleus* protease), plant proteases, recombinant proteases (e.g., produced via recombinant DNA technology by a suitable host cell, selected from any one of bacteria, yeast, fungi, plant, insect or mammalian host cells in culture, or recombinant proteases, which include an amino acid sequence that is homologous or substantially identical to a naturally occurring sequence, proteases encoded by a nucleic acid that is homologous or substantially identical to a naturally occurring protease-encoding nucleic acid, etc.), chemically modified proteases, and mixtures thereof.

The pancrelipase enzymes of the compositions or oral dosage forms of the compositions of the present invention can include one or more lipases (i.e., one lipase, or two or more lipases), one or more amylases (i.e., one amylase, or two or more amylases), one or more proteases (i.e., one protease, or two or more proteases), as well as mixtures of these enzymes in different combinations and ratios. In certain embodiments, the ratio of amylase/lipase activities in the compositions can range from about 1 to about 10, such as from about 2.38 to about 8.75 (e.g., determined by enzymatic assays performed according to LISP protocols). In yet another embodiment, the ratio of protease/lipase can range from about 1 to about 8, such as from about 1.86 to about 5.13 (determined by enzymatic assays performed according to USP protocols). In still other embodiments, the ratio of amylase/lipase activities is about 1, about 2, about 3, about 4, about 5, about 6, about 7, about 8, about 9, or about 10.

Lipase activities in the compositions or oral dosage forms of the present invention can be from about 500 to about 5,000 USP units, preferably from about 750 and about 3,000 USP units. In one embodiment of the invention, the lipase activity can range from about 675 to about 825 USP units, the amylase activity from about 1,600 to about 6,575 USP units, and the protease activity from about 1,250 to about 3,850 UST units.

The carrier(s) is/are used in tabletting to increase the bulk of the tablet to a practical size for compression. These ingredients used in the beads of the present invention have the characteristics of excellent carriers for dry blends providing blend flowability and workability and preventing segregation, and provide pancrelipase content uniformity. A well defined particle size distribution is relevant to provide outstanding flow and mixing properties. Moreover the carrier must have low residual moisture content (low "free water" content).

The carrier may be selected from the group consisting of polyols, sugars, sugar alcohols, cellulose, calcium phosphate salts, and amino acids. More specifically, in certain embodiments of the invention the carrier is selected from the group consisting of microcrystalline cellulose, trehalose, inositol, L-proline in anhydrous form, anhydrous dibasic calcium phosphate, lactose anhydrous, lactose monohydrate, isomalt, mannitol and mixtures thereof, as well as other carriers known in the art.

In a particular embodiment of the invention, the carrier has a large particle size. The term "large size" is defined to be greater than 100 μm; particularly from about 100 μm to about 300 μm, and more particularly from about 160 μm, about 180 μm, about 280 μm, inclusive of all ranges and subranges therebetween, e.g., about 160 μm to about 280 μm, about 160 μm to about 180 μm, about 180 μm, to about 280 μm.

Microcrystalline cellulose is a form of cellulose obtained by spray-drying washed, acid-treated cellulose. It is available in several grades that range in average particle size from 20-100 μm. In addition, microcrystalline cellulose having a mean particle size greater than 100 μm (large particle size microcrystalline cellulose) is also available; e.g., large particle size microcrystalline cellulose of about 160 μm or about 180 μm.

In one particular embodiment of the invention the carrier is large particle size microcrystalline cellulose.

The large particle size microcrystalline cellulose may have a moisture content equal to or less than 5%, nominal mean particle size of about 160 μm, mesh size 38: amount retained ≤1.0%, mesh size of 94: amount retained ≤50.0%, mesh size 300: amount retained ≤70.0%. It has preferably a LoD (loss on drying) of not more than 3.8%.

In another embodiment, the large particle size microcrystalline cellulose may have a moisture content equal to or less than 5%, nominal mean particle size of about 180 μm, mesh size 60: amount retained ≥10.0%, mesh size of 100: amount retained ≥50.0%. It has preferably LoD not more than 1.5%.

In a further embodiment, the microcrystalline cellulose having a moisture content equal to or less than 5%, nominal mean particle size of about 50 μm, mesh size 60: amount retained ≤1.0%, mesh size of 200: amount retained ≤30.0% is used in very low amount (such as about 5.8% by weight of total carrier weight) in admixture with the microcrystalline cellulose having a larger particle size.

Another suitable carrier may be hydrated or anhydrous trehalose (α-D-glucopyranosyl-α-D-glucopyranoside, which is a naturally occurring, non-reducing disaccharide. It is found, for example, in the blood of insects, in fungi, in certain yeasts, and in certain drought-resistant plants. It can be manufactured by fermentation of certain strains of yeast. Trehalose is sweet tasting, and has been suggested for use as a sweetener having reduced cariogenicity in chewing gum and the like. Trehalose is normally manufactured and used as the crystalline dehydrate. Amorphous particulate trehalose may have particle size in the range of about 180 μm to about 280 μm. A particular trehalose used according to the invention is trehalose in its 9.5% dihydrate form, having a low hygroscopic profile. The marketed trehalose used in one embodiment of the present invention is Trehalose G.

Other examples of carriers suitable for use in the present invention are inositol, L-proline in anhydrous form, anhydrous dibasic calcium phosphate (LoD of 0.1-0.2%), lactose, anhydrous lactose (monohydrate with LoD: 4.5-5.5%), and isomalt (LoD of 0.12%).

In the compositions of present invention one single carrier may be used but also a combination of two or more different carriers may be used.

In one embodiment of the invention, only large particle size microcrystalline cellulose is used.

In another embodiment, a binary blend of microcrystalline cellulose and trehalose is used.

In a further embodiment, a blend of two celluloses is used.

In another embodiment of the present invention, the carrier is a mixture of 1:1 w/w of microcrystalline cellulose having a moisture content equal to or less than 5%, nominal mean particle size of about 160 μm, mesh size 38: amount retained ≤1.0%, mesh size 94: amount retained ≤50.0%, mesh size 300: amount retained ≤70.0%, and trehalose.

In another embodiment of the present invention, the carrier is a mixture of 1:1 w/w of microcrystalline cellulose having a moisture content equal to or less than 5%, nominal mean particle size of about 180 μm, mesh size 60: amount retained ≥10.0%, mesh size of 100: amount retained ≥50.0%, and trehalose.

In another embodiment, the carrier is a mixture of 1:1 w/w of two microcrystalline cellulases (MC); one MC having a moisture content less than 5%, nominal mean particle size of about 160 μm, mesh size 38 amount retained ≤1.0%, mesh size of 94, amount retained ≤50.0%, mesh size 300: amount retained ≤70.0%, and the other MC having a moisture content equal to or less than 5%, nominal mean particle size of about 180 μm, mesh size 60 amount retained ≥10.0%, mesh size of 100, amount retained ≥50.0%.

In another embodiment the carrier is a mixture of 16:1 w/w of two microcrystalline celluloses; respectively the first MC having moisture content less than 5%, nominal mean particle size of about 160 μm, mesh size 38: amount retained ≤1.0%, mesh size of 94: amount retained ≤50.0%, mesh size 300: amount retained ≤70.0%, and the other MC having a moisture content equal to or less than 5%, nominal mean particle size of about 50 μm, mesh size 60: amount retained ≤1.0%, mesh size of 200: amount retained ≤30.0%.

The blends comprising pancrelipase and carrier/s and optionally further excipients must have excellent flow properties and consistent particle size. The flow characteristics should enable the loading of the tablet die without difficulty. A sieving procedure can be incorporated to ensure a more controlled even particle size. This is important to guarantee thorough mixing of the components and final homogeneity of the blend.

In addition to the digestive enzymes and the carrier, the beads of the compositions or oral dosage forms of the present invention can further comprise one or more pharmaceutically acceptable excipients. In one embodiment of the invention the amount of excipient is about 5% w/w of the blend. The term "excipients" includes other pharmaceutically acceptable ingredients added to the active component (s) of a composition (e.g., the diluted digestive enzymes) in order to improve processing, stability, palatability, etc. Non-limiting examples of suitable excipients include pharmaceutically acceptable binders, stabilizers, disintegrants, lubricants, glidants, diluents, dyes (coloring agents), stabilizers and mixtures thereof etc. It will be appreciated by those skilled in the art of pharmaceutical formulations that a particular excipient may carry out multiple functions in the composition. The excipients can have a low moisture content, in particular the excipients should have very low "free water" content (less than 15%, less than 10%, about 3% or less). The "free water" is the unbound water.

Non-limiting examples of suitable binders and diluents include starches, modified celluloses (e.g., hydroxypropylcellulose, carboxymethylcellulose sodium), alginic acid, polyvinyl pyrrolidone (povidone), amino acids (proline) and mixtures thereof.

Non-limiting examples of suitable disintegrants include dibasic calcium phosphate, dibasic calcium phosphate dihydrate, tribasic calcium phosphate, alginic acid, hydroxypropylcellulose (such as HPC), carboxymethylcellulose calcium, carboxymethylcellulose sodium, cross-linked carboxymethylcellulose sodium, swellable ion exchange resins, alginates, formaldehyde-casein, cellulose, croscarmellose sodium (e.g., Ac-Di-Sol®), crospovidone (e.g., cross-linked polyvinyl pyrrolidone) (e.g., Kollidon®, CL, Polyplasdone® XL, Polyplasdone® XL-10), sodium carboxymethyl starch, sodium starch glycolate (e.g. Explotab®, Explotab® CV), starches (corn starch, rice starch, maize starch), and mixtures thereof. These disintegrants have low amount of moisture, content (LoD), preferably less than 15%, even more preferably less than 10%, for example croscarmellose sodium may have LoD of less than 15%, sodium starch glycolate may have LoD of about 7-10%, maize starch may have LoD of less than 15%.

Non-limiting examples of suitable lubricants include calcium stearate, magnesium stearate, sodium stearyl fumarate, stearic acid, zinc stearate, talc, waxes, Sterotex®, Stearowet®, and mixtures thereof.

Non-limiting examples of suitable glidants include colloidal silicon dioxide, talc, and mixtures thereof.

Non-limiting examples of suitable stabilizers include trehalose, proline, dextran, maltose, sucrose, mannitol, polyols, silica gel, aminoguanidine, pyridoxamine, and mixtures thereof.

Dyes and coloring compounds such as inorganic or organic pigments may be also added to the blend. Non limiting examples are metal oxides, such as $TiO_2$, $Fe_2O_3$/$Fe_2O$ $3H_2O$, caramel, malt extract (Corocon®), sugar cane (brown sugar). The LoD of metal oxides is less than 1%.

One or more of the excipients used in the present invention can function as a dessicant to further stabilized the composition. Suitable excipients useful as desiccants include any pharmaceutically acceptable excipient that binds water tightly, or reduces the water activity of a composition. For example, the composition of the present invention can include about 1-4% silica gel, or about 2.5% silica gel, anhydrous proline or trehalose.

In one embodiment of the present invention the enterically coated beads comprise about 15 wt. % of pancrelipase, about 80% of the carrier and about 5% of further excipients, wherein each said wt. % is based on the total weight of the uncoated beads.

In another embodiment the enterically coated beads comprise about 10 wt. % pancrelipase, about 85% of the carrier and about 5% of further excipients, wherein each said wt. % is based on the total weight of the uncoated beads.

The diluted pancrelipase beads of the invention may have an enteric coating comprising about 10 to about 20 wt. % of at least one enteric polymer wt. % based on the total weight of the coated beads. Non-limiting examples of gastro-resistant—enteric polymers are cellulose acetate phthalate, hydroxypropylmethylcellulose phthalate, hydroxypropylmethylcellulose acetate succinate, polyvinylacetate phthalate, copolymers of methacrylic acid, esters of methylmethacrylate, and shellac. These polymers are commercially available with different brand names, such as: Cellacefate® (cellulose acetate phthalate), Eudragit® L100, S100, L30D, FS30D, L100-55 (copolymers of methacrylic acid), Aquateric® (cellulose acetate phthalate), Aqoat® (hydroxypropyl methylcelluloacetate succinate), HP55® (hydroxypropyl methylcellulose phthalate).

The coating may further comprise stabilizing agents. Other optional ingredients of the coating are plasticizers, anti-sticking agents, inorganic compound (such as talc, magnesium stearate, colloidal silicon dioxide and combinations thereof); further optionally a low viscosity ethylcellulose). Non-limiting examples of suitable plasticizers include triacetin, tributyl citrate, triethyl citrate, acetyl tri-n-butyl citrate, diethyl phthalate, dibutyl sebacate, polyethylene glycol, polypropylene glycol, castor oil, acetylated mono- and di-glycerides, cetyl/myristil alcohol, and mixtures thereof. The preferred plasticizer is a non-phthalate plasticizer or mixtures thereof of two or more (preferably two) of the listed plasticizers in any combinations.

The inorganic material can include, for example, silicon dioxide, sodium salts, calcium salts, magnesium salts, aluminum salts, aluminum hydroxides, calcium hydroxides magnesium hydroxides, talc, and combinations thereof. In one embodiment, this material is talc.

Depending on the intended use of the composition, the ratio of the enteric polymer and the at least one inorganic material may be in a range of from about 10:1 to about 1:60 by weight. In another embodiment, the ratio of the enteric polymer and the at least one inorganic material ranges from about 8:1 to about 1:50 by weight. In another embodiment, the ratio of the enteric polymer and the at least one inorganic material ranges from about 6:1 to about 1:40 by weight. The ratio of the enteric polymer and the at least one inorganic material may range from about 5:1 to about 1:30 by weight, preferably the ratio of the enteric polymer and the at least one inorganic material ranges from about 4:1 to about 1:25 by weight or from about 4:1 to about 1:9 by weight. The ratio of the enteric polymer and the at least one inorganic material may range from about 10:4 to about 10:7 by weight. The inorganic material of the enteric coating comprises about 1 to about 10% by weight of the weight of the total weight of the particles. In another embodiment the inorganic material comprises about 3, about 5, about 7, or about 10% by weight of the particles. When the inorganic material is talc, it comprises about 20 to about 60% of the dry coating weight, for example about 20%, about 25%, about 30%, about 35%, about 40%, about 45%, about 50%, about 55%, or about 60% of the dry coating weight (inclusive of all ranges, sub-ranges, and values therebetween). In a preferred embodiment, the inorganic compound is talc. In still another particular embodiment, the dry coating of the particles comprises about 31% talc.

In one embodiment of the invention, the coating comprises about 10 to about 20% of a least one enteric polymer, about 4 to about 10% of a least one inorganic compound, and about 1 about 2% of at least one plasticizer (based on the total weight of the particles). For example, the coating can comprise about 10 to about 20% of hydroxypropylmethylcellulose phthalate, about 4 to about 10% of talc, and about 1 to about 2% of triethyl citrate (based on the total weight of the particles).

The coating can be applied to the diluted digestive enzyme-containing beads as a solution of the enteric polymer (and optionally a suspended inorganic material) in an organic solvent such as an alcohol (e.g. ethanol, isopropyl alcohol), a ketone (e.g. acetone), methylene chloride, or mixtures thereof (e.g. mixtures of acetone and ethanol), In a preferred embodiment the hydroxypropylmethylcellulose phthalate is the enteric polymer and acetone is the solvent.

The coated diluted digestive enzyme-containing beads can then be formulated into any suitable oral dosage form. The preferred dosage forms of the present invention are the capsules. The capsules themselves can be comprised of any conventional biodegradable material known in the art, for example, gelatin, polysaccharides such as pullulan, or modified cellulosic materials such as hydroxypropylmethylcellulose. In order to improve the stability of the stabilized digestive enzymes, the capsule can be dried prior to filling, or a capsule comprised of a low moisture content material can be selected. In a preferred embodiment, the capsule shell is comprised of hydroxypropylmethylcellulose and has a water content of about 5% or less, for example about any of 4% or less, 2% or less, or 2-5%, or 3-5%, preferably having a water content of less than about 3% even preferably less than 2%.

The term "moisture content", also referred to as "water content", means the amount of water that a composition contains. For compositions that do not change volume with changing moisture content, the moisture content can be expressed volumetrically (i.e., by volume) as the ratio of the mass of moisture to the dry volume of the material. For compositions that change volume with changing moisture content, the moisture content can be expressed gravimetrically (i.e., by weight) as the mass of water removed upon drying per unit dry mass of the specimen. Determination of moisture content can be achieved by any of the conventional methods known in the art. For example, the moisture content can be determined by chemical titration, such as Karl Fischer titration, in which a sample is dissolved in an electrochemical titration cell. Water from the sample is consumed in an electrochemical reaction whose endpoint is measured potentiometrically, thereby providing a direct measure of the amount of water in the sample. Alternatively, relatively simple thermogravimetric methods may be used such as "Loss on Drying" (LoD), in which the mass of a sample is measured prior to, and after controlled drying. The loss of mass after drying is attributed to loss of moisture. Commercially available moisture analyzers (e.g., available from Mettler Toledo, Sartorius AG, etc.) can also be used to determine moisture content.

The moisture content of the ingredients and of the compositions or oral dosage forms of the present invention can be measured by any suitable method known in the art, for example LoD, or thermogravimetric analysis. LoD is the preferred method.

The compositions or oral dosage forms of the present invention, comprising at least one digestive enzyme, may have a water activity of about 0.6 or less, about 0.5 or less, about 0.4 or less, about 0.3 or less, about 0.2 or less, or about 0.1 or less, inclusive of all ranges and subranges therebetween (i.e., any of about 0.5 to about 0.6, about 0.4 to about 0.6, about 0.3 to about 0.6, about 0.2 to about 0.6, about 0.1 to about 0.6, about 0.4 to about 0.5, about 0.3 to about 0.5, about 0.2 to about 0.5, about 0.1 to about 0.5, about 0.3 to about 0.4, about 0.2 to about 0.4, about 0.1 to about 0.4, about 0.2 to about 0.3, about 0.1 to about 0.3, about 0.1 to about 0.2, etc.). Compositions or oral dosage forms of the present invention, maintained at a low water activity, have been found to be substantially more stable compared to conventional digestive enzymes compositions maintained at higher water activity levels.

Water activity, also referred to as "aw", is the relative availability of water in a substance. As used herein, the term "water activity" is defined as the vapor pressure of water in a sample divided by the vapor pressure of pure water at the same temperature. Pure distilled water has a water activity of exactly one. Water activity is temperature dependent. That is, water activity changes as the temperature changes. In the present invention, water activity is measured at a temperature ranging from about 0° C. to about 50° C., preferably from about 10° C. to about 40° C.

The water activity of a product can be determined by measuring the relative humidity of the air surrounding the sample at equilibrium. Accordingly, measurement of water activity in a sample is typically carried out in an enclosed (usually insulated) space where this equilibrium can take place. At equilibrium, the water activity of the sample and the relative humidity of the air are equal, and therefore a measurement of the equilibrium relative humidity (ERH) of the air in the chamber provides a measure of the water activity of the sample. At least two different types of water activity instruments are commercially available. One type of water activity instruments uses chilled-mirror dew point technology (e.g., AquaLab® water activity meters available from Decagon Devices, Inc.) while others measure relative humidity with sensors that change electrical resistance or capacitance (e.g., water activity meters available from Rotronic®). The water activity of the compositions or oral dosage forms of the present invention can be measured by any suitable method known in the art.

The compositions or dosage forms of the present invention, comprising at least one stabilized digestive enzyme show no loss of enzymatic activity after three months of accelerated stability testing. The composition or dosage form may exhibit a loss of enzyme activity of no more than about 25%, no more than about 20%, no more than about 15%, no more than about 12%, no more than about 10%, no more than about 8%, or no more than about 5%, after six months of accelerated stability testing.

The term "accelerated stability testing" or "accelerated storage testing" refers to test methods used to simulate the effects of relatively long-term storage conditions on enzyme activity, which can be carried out in a relatively short time. Accelerated stability testing methods are known in the art to be a reliable alternative to real-time stability testing, and can accurately predict the shelf life of biological products. Such "accelerated stability testing" conditions are, known in the art and are in accordance with the International Conference for Harmonization of Technical Requirements for Registration of Pharmaceuticals for Human Use: Stability Testing of New Drug Substances and Products Q1A, herein incorporated by reference in its entirety.

After storage (or periodically during storage) the enzyme activity of the samples can be tested using conventional methods for assaying digestive enzyme activity (e.g., U.S. Pharmacopoeia, Pancrelipase: Assay for lipase activity herein incorporated by reference in its entirety).

The compositions of the present invention, and dosage forms comprising the compositions of the present invention, have high stability compared to conventional digestive enzymes (e.g., pancrelipase) compositions and dosage forms and deliver the clinically useful amount of digestive enzyme to a patient, comprising infants or newborns.

The composition or dosage form (e.g., tablet or capsule) of the present invention can be stored in any suitable package. For example, the package can be a glass or plastic jar with a threaded or press-fit closure. Alternatively, the compositions or dosage forms of the present invention can be packaged as a unit dosage form in "blister packs". Improved stability of the digestive enzyme compositions or dosage forms can be provided by providing a moisture-proof seal, and/or a moisture-proof package. Non-limiting examples of suitable moisture-proof packages include glass jars, plastic jars incorporating moisture barrier resins or coatings, aluminized plastic (e.g., Mylar) packaging, etc. The term "moisture-proof" refers to a package which has permeability to water of less than about 0.5 mg water per $cm^3$ of container volume per day.

Containers (e.g., bottles) can be closed with any suitable closure, especially closures which minimize the ingress of moisture during storage. For example, the compositions or dosage forms of the present invention can be thermosealed aluminum liners and polyethylene foam cap liners. In order to ensure package integrity and minimize moisture ingress during storage, sealed packages containing the compositions or dosage forms of the present invention can be leak-tested after dispensing the composition or dosage form of the present invention and sealing the package. For example, the sealed packages can be tested by applying a controlled vacuum to the closure, and detecting the decrease in vacuum over time. Suitable leak-testing equipment includes those manufactured by Bonfiglioli (e.g., model LF-01-PKV or model PKV 516).

Packages containing the compositions or dosage forms of the present invention can also contain a desiccant (i.e., a substance which absorbs, reacts with, or adsorbs water) capable of reducing the humidity inside the package, for example a desiccant, capable of "scavenging" moisture from the atmosphere sealed inside the package. Non-limiting examples of suitable desiccants that can be placed inside such packages include zeolites (e.g., molecular sieves such as 4 A molecular sieves), clay (e.g., montmorillonite clay), silica gel, or combinations thereof. In one embodiment, the desiccant comprises molecular sieves.

In addition, it is common practice when packaging oral pharmaceutical unit doses to add a "plug" of a cellulosic material, such as cotton, into the top of the container to fill the empty space at the top of the container, thereby minimizing movement of the contents. Cellulosic materials are somewhat hygroscopic, and can act as a "reservoir" of moisture inside the package. Accordingly, in the present invention, no cellulosic or cotton "plug" is added. One embodiment of the present invention is the process of preparation of the composition and dosage form with low and uniform pancrelipase content that comprises the following steps:

a) mixing the at least one digestive enzyme and at least one carrier or mixture thereof and optional further excipients to form a mixture; the mixing is carried out under mild condition (such as manual grinding in mortar); high energy milling should be avoided to reduce the risk of lipase activity reduction;

b) direct compressing the mixture into beads;

c) coating the beads with a solution comprising at least one enteric polymer.

The process further comprises the following steps:

d) preparing the dosage forms with the coated beads, such as filling capsules with the coated beads;

e) packaging the dosage forms.

It is highly relevant that all process steps are conducted under strict control of environmental moisture, which should be kept at a very low level; for examples the absolute moisture of incoming air during coating should be kept at values of about 2 to about 3 g/kg, relative humidity during step d) should be less than 40%. Moreover, all ingredients of the blend and of the coating should also have very low moisture content (or preferably less than about 15, or less than about 10%, or less than about 5%, or less than about 3%). The capsule shell should also have low moisture content (less than about 5%, preferably less than about 3%) to minimize water transfer to the product. The packaging configuration should also be carefully chosen in order minimize water permeability. Only under these circumstances do the final diluted digestive enzyme compositions or dosage forms have prolonged storage stability.

Several dosage formulations can be made in which different dimensions of the tablets are obtained, A pancrelipase blend containing the pancrelipase, the carrier(s) and the additional excipients can be tabletted for example using round 2 mm diameter beveled punches, or with round 1.5 mm diameter, 1.2 mm radius of curvature punches to produce microtablets with different dimensions. The blend may be tabletted using compression parameters suitable to obtain pancrelipase minitablets or microtablets. For example, diluted pancrelipase microtablets can be produced according to this invention with weight of about 2 mg to about 4 mg, preferably from about 2.6 to about 3.64 mg, with friability lower than about 2.5% p/p (USP method) and with thickness from about 1.5 to about 2.0 mm.

One embodiment of the present invention provides a method of treating or preventing a condition or disorder associated with digestive enzyme deficiency in a patient, comprising administering the pharmaceutical composition or dosage form of the present invention to a patient (e.g., a mammal such as a human) in need thereof.

In another embodiment, the invention provides a method of treating or preventing a disorder or condition associated with digestive enzyme deficiency, comprising administering the composition or dosage form of the present invention to a patient in need thereof, wherein the composition or dosage form comprises, in addition to the digestive enzymes, at least one proton pump inhibitor, or one antacid, or other medicament which increases GI pH. In still another embodiment, the present invention provides a method of treating or preventing a disorder or condition associated with digestive enzyme deficiency, comprising administering a composition or dosage form of the present invention, in combination with a dosage form comprising at least one proton pump inhibitor, one antacid, or other medicament which increases GI pH.

Disorders or conditions that can be treated with the composition or dosage forms of the present invention include conditions in which the patient has no or low levels of digestive enzymes or in which patients require digestive enzyme supplementation. For example, such conditions can include exocrine pancreatic insufficiency, cystic fibrosis, chronic pancreatitis, other pancreatic diseases (e.g., hereditary, post-traumatic and allograft pancreatitis, hemochromatosis, Shwachman syndrome, lipomatosis, or hyperparathyroidism), side-effects of cancer or cancer treatment, side-effects of surgery (e.g., gastrointestinal bypass surgery, Whipple procedure, total pancreatectomy, etc.) or other conditions in which pancreatic enzymes cannot reach the intestine, poor mixing (e.g., Billroth II gastrectomy, other types of gastric bypass surgery, gastrinoma, etc.), side effects of drug treatments such as treatment with metformin or those drugs used to treat the symptoms of HIV and autoimmune diseases such as diabetes in which the pancreas may be compromised, obstruction (e.g., pancreatic and biliary duct lithiasis, pancreatic and duodenal neoplasms, ductal stenosis), malabsorption associated with celiac disease, food allergies and aging.

Particularly relevant for the purpose of present invention is the treatment of newborns and infants in need of treatment thereof with the diluted composition or dosage form of the present invention.

The term "pharmaceutically effective amount" refers to an amount of composition of the invention or dosage form thereof, as disclosed herein, effective in reducing or ameliorating conditions or symptoms associated with pancreatic enzyme insufficiency in a patient.

In one embodiment of the invention, an effective amount of the compositions or dosages forms herein disclosed are administered in the treatment of pancreatic enzyme replacement therapy (PERT) in CF (cystic fibrosis) newborns or infants with symptomatic or confirmed pancreatic insufficiency or exocrine pancreatic insufficiency. The compositions or dosage forms are administered for improving coefficient of fat absorption (CFA).

From the foregoing description and the experiments disclosed herein, it can be seen that the present invention provides several important advantages. The described invention provides diluted pancrelipase compositions and dosage forms characterized by high content uniformity and stability, and the composition and dosage forms herein are therefore suitable for use with infants and newborns who need low doses of pancreatic enzymes.

It is to be understood that both the general description and the detailed description herein are exemplary, but not restrictive of the invention, and that all embodiments can naturally be combined with one another.

EXAMPLES

Methods

Dissolution test a) Acid stage medium (pH 1.2): Place 2.00 g of sodium chloride in 800 mL purified water and stir until complete solubilization. Add 7 mL 37% HCl and mix. Adjust the pH of the solution to 1.20±0.05 with 1 N HCl or 1 N NaOH. Dilute to 1000 mL with purified water; check the pH and adjust to 1.20±0.05 with 1 N HCl or 1 N NaOH, if needed, b) Enteric stage medium (pH 6.0): Place 9.20 g monobasic potassium phosphate and 2.00 g sodium chloride in 800 mL purified water and stir until complete solubilization. Adjust the pH of the solution to 6.00±0.05 with 1 N NaOH. Dilute to 1,000 mL with purified water; check the pH and adjust to 6.00±0.05 with 1 N HCl or 1 N NaOH, if needed.

The measurement of lipolytic activity is carried out using a method based on the compendia procedure of lipase assay described in the pancrelipase USP monograph, which is based on the titration, by means of pH-stat method, of the free fatty acids formed from the hydrolysis of esterified fatty acids in the substrate used (olive oil). It is based on the following principle: lipase catalyses the hydrolysis of the triglycerides which leads to the formation of free fatty acids (HA), The titration of the formed FFA according to time provides for the determination of the enzymatic activity of lipase, which can be expressed in units: 1 U=1 µmole of formed FFA per minute. The reaction occurs by maintaining a steady pH value through an experimental system that provides for the addition of NaOH (titrant) when the pH value changes compared to a fixed value (pHstat method). The quantity of added titrant according to time corresponds to the quantity of FFA formed by the lipase action on the triglycerides. Provided that the procedure is carried out with a suitable quantity of substrate and under experimental conditions where the enzyme is stable, linear kinetics for the FFA formation according to time can be obtained. The curve slope {added titrant=f (volume (mL)/time (minutes))} gives the lipase enzymatic activity.

The measurement of proteolytic activity is carried out according to the compendia procedure described in the pancrelipase USP monograph.

Example 1. Pancrelipase—Carrier Blends Compatibility

Binary blends of pancrelipase and carrier arc prepared by mixing to ascertain the stability of the pancrelipase in presence of said ingredients. This binary blend contains pancrelipase in amount of 60 mg and the carrier in amount of 324 mg; the tested carriers arc: microcrystalline cellulose (microcrystalline cellulose C: moisture content equal or less than 5%, nominal mean particle size of 50 µm, mesh size 60: amount retained ≤1.0%, mesh size of 200: amount retained ≤30.0%; marketed as Avicel®PH101), trehalose, lactose monohydrate, isomalt, proline inositol. The samples are packaged in 10 mL PET and glass vials in the absence of desiccant. They are stored under two different conditions: mild storage condition (25° C., 65% relative humidity (RH)) and aggravated storage conditions (40° C., 75% relative humidity). Lipase activity is tested after different periods of storage according to the compendia method described herein.

TABLE 1

Lipase activity of the blends stored at 25° C./65 RH, PET vials (lipase activity of the blends is calculated as % of the lipase activity of the pancrelipase sample)

|  | Carrier | Storage time | | | |
|---|---|---|---|---|---|
|  |  | 0 | 1 week | 2 weeks | 4 weeks |
| Pancrelipase (USP units lipase) | none | 95 | 94 | 90 | 80 |
| Pancrelipas | Cellulose microcrystalline C | 98 | 100 | 99 | 103 |
| Pancrelipase | Trehalose | 100 | 99 | 99 | 98 |
| Pancrelipase | Lactose monohydrate | 99 | 100 | 98 | 98 |
| Pancrelipase | Anhydrous dibasic calcium phosphate | 93 | 98 | 96 | 100 |
| Pancrelipase % | Isomalt | 100 | 98 | 94 | 99 |
| Pancrelipase % | Proline | 100 | 101 | 99 | 87 |
| Pancrelipase % | Inositol | 100 | 97 | 96 | 103 |

TABLE 2

Lipase activity of the blends stored at 25° C./65 RH, glass vials (lipase activity of the blends is calculated as % of the lipase of the activity pancrelipase sample)

|  | Carrier | Storage time | |
|---|---|---|---|
|  |  | 0 | 1 week |
| Pancrelipase (USP units lipase) | None | 95 | 94 |
| Pancrelipase | Cellulose microcrystalline C | 98 | 98 |
| Pancrelipase | Trehalose | 100 | 99 |
| Pancrelipase | Lactose monohydrate | 99 | 97 |
| Pancrelipase | Anhydrous dibasic calcium phosphate | 93 | 102 |
| Pancrelipase | Isomalt | 100 | 97 |

TABLE 3

Lipase activity of the blends stored at 40° C./75 RH, PET vials (lipase activity of the blends is calculated as % of the lipase activity of the pancrelipase sample)

|  | Carrier | Storage time | | | |
|---|---|---|---|---|---|
|  |  | 0 | 1 week | 2 weeks | 4 weeks |
| Pancrelipase (USP units lipase) | None | 95 | 96 | 48 | 315 |
| Pancrelipase % | Cellulose microcrystalline C | 98 | 103 | 113 | 113 |
| Pancrelipase % | Trehalose | 100 | 97 | 100 | 106 |
| Pancrelipase % | Lactose monohydrate | 99 | 99 | 106 | 113 |
| Pancrelipase % | Anhydrous dibasic calcium phosphate | 93 | 99 | 106 | 113 |
| Pancrelipase % | Isomalt | 100 | 96 | 102 | 100 |
| Pancrelipase % | Inositol | 100 | 101 | 110 | 106 |

Example 2. Physical Characterization of the Pancrelipase—Carrier Blends

Pancrelipase is blended with one or more carriers and the physical characterization of these mixture is carried out by measuring the density (both bulk and tapped), the Carr index (compactability index), the flowability (flow rate through an orifice is measured as the mass per time flowing from funnel, USP method), the LoD. The summary of the results is reported in Table 4.

TABLE 4

| Batch | Density | | % Carr index | Mass flow g/sec (100 g) | | | | T = 0 | LoD % | | | |
|---|---|---|---|---|---|---|---|---|---|---|---|---|
|  | untapped | tapped |  | ⌀ 10 mm g/s | ⌀ 15 mm g/s | ⌀ 20 mm g/s | ⌀ 30 mm g/s |  | 24 h/ room temp; closed vial | 24 h/ room temp; open vial | 72 h/ room temp; closed vial | 72 h/ room temp; open vial |
| Reference sample[4] | 0.657 | 0.781 | 15.88 | 7.1 | / | / | / | 0.96 | 1.51 | 2.69 | / | / |
| Microcrystalline cellulose C[3] | 0.438 | 0.561 | 21.93 | No flow | No flow | No flow | 20.8 | 3.68 | 4.05 | 4.04 | / | / |
| Microcrystalline cellulose B[2] | 0.423 | 0.500 | 15.40 | 10.4 | / | / | / | 1.09 | 1.59 | 2.12 | / | / |
| Trehalose G | 0.757 | 0.892 | 15.13 | 5.9 | / | / | / | 6.45 | 6.72 | 6.52 | / | / |
| Lactose Monohydrate | 0.549 | 0.632 | 13.13 | 7.1 | / | / | / | 0.43 | 0.71 | 0.87 | / | / |
| L-Proline | 0.512 | 0.581 | 11.88 | 4.5 | / | / | / | 0.43 | / | / | 0.52 | 0.97 |
| Calcium Bibasic | 0.694 | 0.806 | 13.90 | 9.1 | / | / | / | 0.70 | / | / | 0.89 | 1.25 |
| Isomalt | 0.434 | 0.500 | 13.20 | 5.5 | / | / | / | 2.55 | / | / | 2.57 | 2.84 |
| Anhydrous lactose | 0.769 | 0.833 | 7.68 | 4.34 | / | / | / | 0.43 | / | / | 0.51 | 0.86 |
| Microcrystalline cellulose A[1] | 0.434 | 0.515 | 15.73 | 4.34 | / | / | / | 3.89 | 3.92 | 3.96 | / | / |
| Inositol | 0.609 | 0.781 | 22.02 | 6.66 | / | / | / | 0.61 | / | / | 0.45 | 0.93 |
| Microcrystalline cellulose B[2] + C[3] blends (1:1) | 0.442 | 0.549 | 19.49 | No flow | 5.88 | / | / | 2.72 | 2.8 | 2.91 | / | / |

TABLE 4-continued

| | | | | Mass flow g/sec (100 g) | | | | | LoD % | | | |
| | Density | | % Carr index | ⌀ 10 mm | ⌀ 15 mm | ⌀ 20 mm | ⌀ 30 mm | | 24 h/ room temp; closed vial | 24 h/ room temp; open vial | 72 h/ room temp; closed vial | 72 h/ room temp; open vial |
| Batch | untapped | tapped | | g/s | g/s | g/s | g/s | T = 0 | | | | |
|---|---|---|---|---|---|---|---|---|---|---|---|---|
| Microcrystalline cellulose A[1] + C[3] (1:1) | 0.454 | 0.568 | 20.07 | No flow | 14.28 | / | / | 3.36 | 4.17 | 4.17 | / | / |
| Microcrystalline cellulose C[3] + Trehalose G (1:1) | 0.561 | 0.724 | 22.51 | No flow | 8.33 | / | / | 2.78 | 5.64 | 5.86 | / | / |
| Microcrystalline cellulose C[3] + L-Proline (1:1) | 0.515 | 0.649 | 20.65 | No flow | 12.5 | / | / | 2.39 | 2.19 | 2.18 | / | / |
| Microcrystalline cellulose C[3] + Lactose anhydrous (1:1) | 0.555 | 0.684 | 18.86 | No flow | 3.33 | / | / | 2.07 | 2.27 | 2.15 | / | / |
| Microcrystalline cellulose C[3] + Lactose Monohydrate (1:1) | 0.521 | 0.657 | 20.70 | No flow | 10.0 | / | / | 1.94 | 2.18 | 2.36 | / | / |
| Microcrystalline cellulose C[3] + Calcium bibasic (1:1) | 0.561 | 0.704 | 20.31 | No flow | 10.5 | / | / | 2.1 | 2.5 | 2.65 | / | |
| Microcrystalline cellulose C[3] + Isomalt (1:1) | 0.510 | 0.609 | 16.26 | No flow | 12.5 | / | / | 3.38 | 3.37 | 3.4 | / | / |
| Microcrystalline cellulose C[3] + Inositol (1:1) | 0.531 | 0.675 | 21.33 | No flow | 6.66 | / | / | 2.29 | / | / | 2.06 | 2.27 |

[A]Reference sample: pancrelipase (90%), croscarmellose sodium (3.0%), hydrogenated castor oil (1.0%), colloidal silicone dioxide (0.5%), microcrystalline cellulose (5%) (Avicel ® PH101); magnesium stearate (0.5%)

TABLE 5

Types of microcrystalline celluloses

| | Nominal mean particle size (μm) | Particle size analysis: Mesh size | Amount retained % | LoD |
|---|---|---|---|---|
| [1]Microcrystalline cellulose A | 160 | 38 | ≤1 | <5% |
| | | 94 | ≤50 | |
| | | 300 | ≤70 | |
| [2]Microcrystalline cellulose B | 180 | 60 | ≥10.0 | <5% |
| | | 100 | ≥50 | |
| [3]Microcrystalline cellulose C | 50 | 60 | ≤1 | <5% |
| | | 200 | ≤30 | |

Crystalline cellulose A is marketed as Vivapure ® 12;
crystalline cellulose B is marketed as Avicel ® LM200;
crystalline cellulose C is marketed as Avicel ® PH101.

From the above Table 4 it can be evinced that the microcrystalline cellulose C (moisture content equal to or less than 5%, nominal mean particle size of 50 μm, mesh size 60: amount retained ≤1.0%, mesh size of 200: amount retained ≤30.0%) has low mass flow which is an indication of critical issues during the direct compression process. To avoid such issues with carriers having low flowability, an additional treatment step (such as wet-granulation) would typically be carried out to increase the mass flow. However, any such additional steps are detrimental to the enzymatic activity of the pancrelipase formulation and therefore should be avoided to reduce the risk of degradation.

Example 3. Hardness Measurements of Tablets of the Pancrelipase—Carrier Blends

Figure 1:
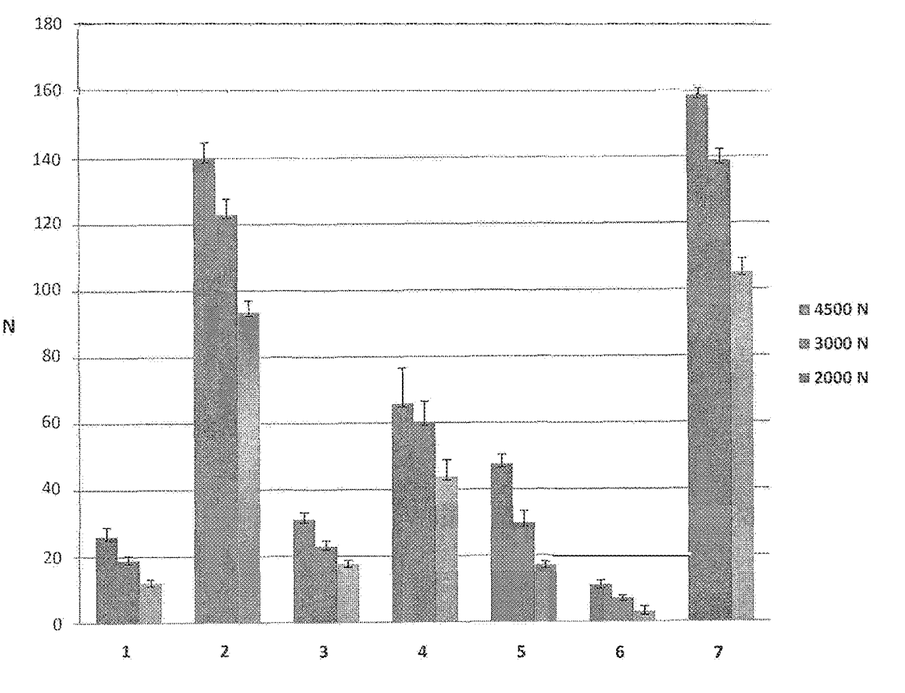
FIG. 1. Hardness of tablets consisting of pancrelipase and a carrier (blend 1: pancrelipase; blend 2: pancrelipase and microcrystalline cellulose B; blend 3: pancrelipase and trehalose; blend 4: pancrelipase and isomalt; blend 5: pancrelipase and calcium bibasic; blend 6: pancrelipase and inostol; blend 7: pancrelipase and microcrystalline cellulose A).

Pancrelipase raw material (e.g., received from Nordmark) is mixed with different carriers to form the seven different blends: blend 1: pancrelipase, blend 2: pancrelipase and microcrystalline cellulose B; blend 3: pancrelipase and trehalose; blend 4: pancrelipase and isomalt; blend 5: pancrelipase and calcium bibasic; blend 6: pancrelipase and inositol, blend 7: pancrelipase and microcrystalline cellulose A. Theses blends are tabletted by direct compression and hardness is measured for each sample. The results are reported in FIG. 1.

Suitable hardness values are very crucial since low hardness is critical during the subsequent step of coating process.

Example 4. Preparation of 15% Diluted Pancrelipase Microtablets

Pancrelipase raw material (e.g., received from Nordmark) is mixed with the carrier(s) and the further excipients to form the different blends. Three different blends are prepared.

The first blend (blend 1) contains: 15% pancrelipase, 80% cellulose microcrystalline A (moisture content less than 5%, nominal mean particle size of 160 μm, mesh size 38: amount retained 1.0%, mesh size 94: amount retained ≤50.0%, mesh size 300: amount retained ≤70.0%), and 5% excipients (croscarmellose sodium, 3.0%; hydrogenated castor oil, 1.0%; colloidal silicone dioxide, 0.5%; magnesium stearate 0.5%), wherein each said wt % is based on the total weight of the blend.

The second blend (blend 2) contains: 15% pancrelipase, 40% cellulose microcrystalline A (moisture content less than 5%, nominal mean particle size of 160 μm, mesh size 38: amount retained 1.0%, mesh size 94: amount retained ≤50.0%, mesh size 300: amount retained ≤70.0%.), 40% trehalose (Trehalose G), 5% excipients (croscarmellose sodium, 3.0%; hydrogenated castor oil, 1.0%; colloidal silicone dioxide, 0.5%, magnesium stearate 0.5%), wherein each said wt % is based on the total weight of the blend.

The third blend (blend 3) contains: 15% pancrelipase, 40% cellulose microcrystalline B (moisture content equal or less than 5%, nominal mean particle size of 180 μm, mesh size 60: amount retained ≥10.0%, mesh size 100: amount retained ≤50.0%), 40% trehalose (trehalose G), 5% excipients (croscarmellose sodium, 3.0%; hydrogenated castor oil, 1.0%; colloidal silicone dioxide, 0.5%; magnesium stearate 0.5%), wherein each said wt % is based on the total weight of the blend.

Microcrystalline celluloses A and B are defined in Table 5 of Example 3.

The three blends are then tabletted to produce microtablets (1.5×1.5 mm). The microtablets are tested for, lipase activity, disintegration time, LoD; their weight, thickness and friability are also measured on each batch produced (Table 6).

TABLE 6

| Test | μtablet 1 (blend 1) | μtablet 2 (blend 2) | μtablet 3 (blend 3) |
|---|---|---|---|
| Lipase (USP units/mg) | 14.6 | 14.9 | 15.3 |
| Disintegration (min) | 3 | 4 | 3 |
| LoD(%) | 2.3 | 1.8 | 2.7 |
| Weight (mean value) (g) | 0.0034 | 0.0035 | 0.0035 |
| Thickness*(mean value) (mm) | 1.51 | 1.48 | 1.50 |
| Friability* (mean value) (%) | 1.1 | 1.2 | 1.3 |

*USP method (20 g of MT, 30 min at 25 rpm)

The above μtab has high homogeneity in terms of pancrelipase content (CV % below 5%).

Example 5. Preparation of 10% Diluted Pancrelipase Minitablets

Pancrelipase raw material (e.g. obtained from Nordmark) and carrier microcrystalline cellulose) and excipients croscarmellose sodium, hydrogenated castor oil, colloidal silicon dioxide, microcrystalline cellulose, and magnesium stearate) mixed to form a blend. The composition of the blend is reported in the following table (Table 7), and has a density of 0.75-0.76 g/ml.

TABLE 7

| Component | Kg (theoretical) for 1 batch | % |
|---|---|---|
| Microcrystalline cellulose A | 297.6 | 80 |
| Pancrelipase | 37.2 | 10 |
| Croscarmellose sodium | 11.16 | 3 |
| Hydrogenated castor oil | 3.72 | 1 |
| Colloidal silicon dioxide | 1.86 | 0.5 |
| Microcrystalline cellulose C | 18.6 | 5 |
| Magnesium stearate 0.3-0.4 g/ml | 1.86 | 0.5 |
| Total | 372 | 100 |

Microcrystalline celluloses A and C are defined in Table 5 of Example 3.

The above blend is tabletted using round 2 mm diameter beveled punches; the compression parameters Table 8) are set to obtain pancrelipase minitablets (MTs) having the following physical characteristics: weight between 0.074 g and 0,086 with friability lower than 2.5% p/p (USP method), thickness between 2.0 and 2.4 mm.

TABLE 8

| Compression parameter | 10% pancrelipase MT |
|---|---|
| Tabletting machine speed (rpm) | 20 |
| Forced feeding (rpm) | 20 |
| Average compression force (kN) | about 10 |
| Average pre compression force (kN) | about 10 |
| Dosing chamber parameters (mm) | 5-5.5 |

4 batches (A-D) of the 10% diluted pancrelipase MTs are produced with these blends; they have the following physical properties (Table 9).

TABLE 9

|  | Batch A | Batch B | Batch C | Batch D |
|---|---|---|---|---|
| Weight (mean value) (g) | 0.079 | 0.079 | 0.08 | 0.081 |
| Thickness*(mean value) (mm) | 2.2 | 2.2 | 2.2 | 2.2 |
| Friability* (mean value) (%) | 0.7 | 0.8 | 0.6 | 0.7 |

*USP method (20 g of MT, 30 min at 25 rpm)

Example 6. Content Uniformity of 10% Pancrelipase MTs

The uniformity of the dosage units is demonstrated by measuring the content uniformity. Each batch is prepared as in example 4 and is assayed by measuring the lipase content according to compendia methods for assaying digestive enzymes activity (e.g., United States Pharmacopoeia, Pancrelipase: assay for lipase activity). The assay is repeated 10 times per each batch and the CV % results are reported in Table 10.

TABLE 10

| Batch | Coefficient of variation (%) |
|---|---|
| A | 3.2 |
| B | 2.4 |
| C | 2.0 |
| D | 3.3 |

The MTs prepared show high homogeneity in terms of pancrelipase content. In fact, the requirements for dosage uniformity are met by all assayed batches since the CV % is below 5%.

Example 7. Coating of Diluted Pancrelipase Tablets (μTs and MTs)

The 15% diluted pancrelipase μTs and the 10% diluted pancrelipase MTs (Examples 5 and 6, respectively) are then coated by fluid bed with a coating formulation (having the composition of Table 11) in a coating pan. The coating may be started when the tablets reach temperature of 15-32° C. The composition of the coated particles prepared according to the standard coating method applied for Zenpep® minicabs produces uniform, smooth and homogeneous particles (as analyzed by microscopic examination),

TABLE 11

| Component | % (w/w) |
|---|---|
| Hypromellose phthalate (HP55) | 7.64 |
| Triethyl citrate (TEC) | 0.76 |
| Talc | 3.82 |
| Acetone | 87.78 |
| total | 100.00 |

Hydroxypropylmethylcellulose capsules with very low moisture content are then filled with the coated diluted pancrelipase microtablets.

Example 8. Enzymatic Activity and Dissolution of Enterically Coated Diluted Pancrelipase Formulation HPMC capsules (size 4 white OP/white OP) are filled with diluted enterically coated pancrelipase µTs. The capsules are stored in glass bottle with PP closure-liner, Minipax desiccants. Enzymatic activities are measured on the formulations stored under different conditions (at 25° C. and 60% relative humidity, and at 40° C. and 75% relative humidity) (Tables 13-18). Storage stability of bulk enterically coated diluted pancrelipase microtablets stored at 40° C. and 75% relative humidity in glass bottle with PP closure-liner, Minipax desiccants are also tested (Table 12). The dissolution of the microtablets is also measured.

The enterically coated microtablets 1 (µT1) contains: 15% pancrelipase, 80% cellulose microcrystalline A (moisture content less than 5%, nominal mean particle size of 160 µm, mesh size 38: amount retained ≤1.0%, mesh size 94: amount retained ≤50.0%, mesh size 300: amount retained ≤70.0%), and 5% excipients (croscarmellose sodium, 3.0%; hydrogenated castor oil, 1.0%; colloidal silicone dioxide, 0.5%; magnesium stearate 0.5%), wherein each said wt % is based on the total weight of the uncoated µTs.

The enterically coated microtablets 2 (µT2) contains: 15% pancrelipase, 40% cellulose microcrystalline A (moisture content less than 5%, nominal mean particle size of 160 µm, mesh size 38: amount retained ≤1.0%, mesh size 94: amount retained ≤50.0%, mesh size 300: amount retained ≤70.0%), 40% trehalose, 5% excipients (croscarmellose sodium, 3.0%; hydrogenated castor oil, 1.0%; colloidal silicone dioxide, 0.5%, magnesium stearate 0.5%), wherein each said wt % is based on the total weight of the uncoated µTs.

The enterically coated microtablets 3 (µT3) contains: 15% pancrelipase, 40% cellulose microcrystalline B (moisture content equal or less than 5%, nominal mean particle size of 180 µm, mesh size 60: amount retained ≥10.0%, mesh size 100: amount retained ≥50.0%), 40% trehalose, 5% excipients (croscarmellose sodium, 3.0%; hydrogenated castor oil, 1.0%; colloidal silicone dioxide, 0.5%; magnesium stearate 0.5%), wherein each said wt % is based on the total weight of the µTs.

Microcrystalline celluloses A and B are defined in Table 5 of Example 3; the enteric coating composition is the same as the coating of Example 7 (Table 11).

TABLE 12

Stability of bulk enterically coated diluted pancrelipase microtablets (µTs); storage conditions: 40° C. + 75% relative humidity

| | Lipase activity USP units/mg | | |
|---|---|---|---|
| Batch | Time 0 | Time 3 mo | Diff time |
| µT1 (carrier: microcrystalline cellulose A) | 11.5 | 11.2 | 97 |
| µT2 (carrier: microcrystalline cellulose A and trehalose) | 11.7 | 11.7 | 100 |
| µT3 (carrier, microcrystalline cellulose B and trehalose) | 11.5 | 11.4 | 99 |

TABLE 13

Analysis of enterically coated diluted pancrelipase microtablets, µT1 (carrier: microcrystalline cellulose A); storage conditions: 25° C., 60% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 735 | 761 | 754 | 774 |
| | % label claim | 98 | 101 | 101 | 103 |
| | Diff T0 (%) | | 104 | 103 | 105 |
| protease activity (USP units/cps) | 1,250-3,850 USP units/cps | 2,015 | 2,145 | 2,145 | 2,210 |
| amylase activity (USP units/cps) | 1,600-6,575 USP units/cps | 2,600 | 2,665 | 2,665 | 2,795 |
| Pthalic Actd(%) | NMT 1.4% | 0.1 | 0.1 | 0.1 | 0.1 |
| LoD (%) | NMT 5.0% | 2.4 | 0.5 | 0.1 | 0.3 |
| dissolution (%) 30 min | NLT 75% | 84% (RSD 3.6) | 87% (RSD 2.6) | 85% (RSD 2.1) | 83% (RSD 3.0) |
| dissolution (%) × 1.125 | | 95% (RSD 2.9) | 98% (RSD 2.2) | 96% (RSD 1.5) | 94% (RSD 3.0) |
| Weight n = 10 (mg) | | 65 | 65 | 65 | 65 |

TABLE 14

Analysis of enterically coated diluted pancrelipase microtablets µT1 (carrier: microcrystalline cellulose A); storage conditions: 40° C., 75% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP unis/cps) | 90-110% of label claim 675-825 USP units/cps | 735 | 754 | 754 | 754 |
| | % label claim | 98 | 101 | 101 | 101 |
| | Diff T0 (%) | | 103 | 103 | 103 |

TABLE 14-continued

Analysis of enterically coated diluted pancrelipase microtablets μT1 (carrier: microcrystalline cellulose A); storage conditions: 40° C., 75% relative humidity

| Test | Specification | Time 0 | Time 1 mo | Time 2 mo | Time 3 mo |
|---|---|---|---|---|---|
| protease activity (USP units/cps) | 1,250-3,850 USP units/cps | 2,015 | 2,080 | 2,015 | 2,015 |
| amylase activity (USP units/cps) | 1,600-6,575 USP units/cps | 2,600 | 2,665 | 2,600 | 2,795 |
| Pthalic Acid(%) | NMT 1.4% | 0.1 | 0.1 | 0.1 | 0.1 |
| LoD (%) | NMT 5.0% | 2.4 | 0.4 | 0.1 | 0.2 |
| dissolution (%) 30 min | NLT 75% | 84% (RSD 3.6) | 84% (RSD 2.9) | 83% (RSD 2.2) | 82% (RD 1.8) |
| dissolution (%) × 1.125 | | 95% (RSD 2.9) | 94% (RSD 2.2) | 96% (RSD 2.3) | 93% (RSD 1.8) |
| Weight n = 10 (mg) | | 65 | 65 | 65 | 65 |

TABLE 15

Analysis of enterically coated diluted pancrelipase microtablets μT2 (carrier: microcrystalline cellulose A and trehalose); storage conditions: 25° C., 76% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 736 | 755 | 762 | 755 |
| | % label claim | 98 | 101 | 102 | 101 |
| | Dff T0 (%) | | 103 | 104 | 103 |
| protease activity (USP units/cps) | 1,250-3,850 USP units/cps | 1,984 | 2,048 | 1,984 | 2,112 |
| amylase activity (USP units/cps) | 1,600-6,575 U USP/cps | 2,496 | 2,688 | 2,880 | 2,816 |
| Pthalic Acid(%) | NMT 1.4% | 0.1 | 0.1 | 0.1 | 0.1 |
| LoD (%) | NMT 5.0% | 1.6 | 0.2 | 0.2 | 0.3 |
| dissolution (%) 30 min | NLT 75% | 84% (RSD 2.0) | 91% (RSD 3.6) | 87% (RSD 2.4) | 86% (RD 12.2) |
| dissolution (%) × 1.125 | | 94% (RSD 2.3) | 103% (RSD 3.6) | 98% (RSD 2.5) | 96% (RSD 1.7) |
| Weight n = 10 (mg) | | 64 | 64 | 64 | 64 |

TABLE 16

Analysis of enterically coated diluted pancrelipase microtablets μT2 (carrier: microcrystalline cellulose A and trehalose); storage conditions: 40° C., 75% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 736 | 755 | 781 | 742 |
| | % label claim | 98 | 101 | 104 | 199 |
| | Dff T0 (%) | | 103 | 106 | 101 |
| protease activity (USP units/cps) | 1,250-3,850 USP units/cps | 1,984 | 2,240 | 2,048 | 1,984 |
| amylase activity (USP units/cps) | 1,600-6,575 USP units/cps | 2,496 | 2,688 | 2,880 | 2,688 |
| Pthalic Acid(%) | NMT 1.4% | 0.1 | 0.1 | 0.1 | 0.1 |
| LoD (%) | NMT 5.0% | 1.6 | 0.5 | 0.2 | 0.3 |
| dissolution (%) 30 min | NLT 75% | 84% (RSD 2.0) | 91% (RSD 2.6) | 87% (RSD 3.7) | 84% (RD 1.4) |
| dissolution (%) × 1.125 | | 94% (RSD 2.3) | 103% (RSD 2.7) | 98% (RSD 4.0) | 94% (RSD 1.7) |
| Weight n = 10 (mg) | | 64 | 64 | 64 | 64 |

TABLE 17

Analysis of enterically coated diluted pancrelipase microtablets μT3 (carrier: microcrystalline cellulose B and trehalose); storage conditions: 25° C., 60% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 746 | 770 | 779 | 792 |
| | % label claim | 99 | 104 | 104 | 106 |
| | Dff T0 (%) | | 104 | 104 | 106 |
| protease activity (USP units/cps) | 1,250-3,850 USP units/cps | 1,980 | 2,112 | 2,112 | 2,112 |
| amylase activity (USP units/cps) | 1,600-6,575 USP units/cps | 2,640 | 2,838 | 2,772 | 2,838 |
| Pthalic Acid(%) | NMT 1.4% | 0.1 | 0.1 | 0.1 | 0.1 |
| LoD (%) | NMT 5.0% | 1.6 | 0.5 | 0.2 | 0.3 |
| dissolution (%) 30 min | NLT 75% | 87% (RSD 2.4) | 91% (RSD 2.6) | 89% (RSD 1.4) | 91% (RD 3.4) |
| dissolution (%) × 1.125 | | 98% (RSD 2.1) | 102% (RSD 2.7) | 100% (RSD 1.2) | 103% (RSD 3.4) |
| Weight n = 10 (mg) | | 66 | 66 | 66 | 66 |

TABLE 18

Analysis of enterically coated diluted pancrelipase microtablets µT3 (carrier: microcrystalline cellulose B and trehalose); storage conditions: 40° C., 75% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 746 | 766 | 766 | 766 |
| % label claim | | 99 | 102 | 102 | 102 |
| Dff T0 (%) | | | 103 | 103 | 103 |
| protease activity (USP units/cps) | 1,250-3,850 USP units/cps | 1,980 | 1,980 | 2,046 | 2,046 |
| amylase activity (USP units/cps) | 1,600-6,575 USP units/cps | 2,640 | 2,838 | 2,706 | 2,904 |
| Pthalic Acid(%) | NMT 1.4% | 0.1 | 0.1 | 0.1 | 0.1 |
| LoD (%) | NMT 5.0% | 1.6 | 0.4 | 0.1 | 0.3 |
| dissolution (%) | NLT 75% 30 min | 87% (RSD 2.4) | 89% (RSD 1.0) | 86% (RSD 1.4) | 88% RD 2.4) |
| dissolution (%) × 1.125 | | 98% (RSD 2.1) | 100% (RSD 0.9) | 97% (RSD 1.2) | 99% (RSD 2.1) |
| Weight n = 10 (mg) | | 66 | 66 | 66 | 66 |

The results indicate that the diluted pancrelipase of the invention are highly stable for long period of time even under aggravated conditions of storage.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fail within the broader ranges.

We claim:

1. A process for the preparation of a pharmaceutical composition comprising a blend of at least one digestive enzyme and at least one carrier, the process comprising the following steps:
a) mixing the at least one digestive enzyme and the at least one carrier, and optional further excipients;
b) compressing the mixture into beads; and
c) optionally coating the beads with an enteric polymer, wherein a total amount of the at least one digestive enzyme in the pharmaceutical composition is from 4% to 19% by weight, and the at least one carrier comprises microcrystalline cellulose having an average particle size greater than 100 µm.

2. The process of claim 1, wherein the process comprises step c).

3. The process of claim 1, wherein the steps are carried out in a low moisture environment and the moisture of the carrier or carriers is equal to or less than 5%.

4. The process of claim 2, wherein the at least one digestive enzyme is in the form of enterically coated pancrelipase beads.

5. The process of claim 4, wherein the total amount of the at least one digestive enzyme in the pharmaceutical composition is from 10% to 15% by weight.

6. The process of claim 4, wherein the enterically coated pancrelipase beads comprise from 4 wt. % to 19 wt. % of pancrepliase based on a total weight of uncoated beads and from 70 wt. % to 96 wt. % of the at least one carrier based on the total weight of the uncoated beads.

7. The process of claim 4, wherein the enterically coated pancreplipase beads comprise from 10 wt. % to 15 wt. % of pancrelipase based on a total weight of uncoated beads and from 75 wt. % to 90 wt. % of the at least one carrier based on the total weight of the uncoated beads.

8. The process of claim 4, wherein the enterically coated pancrelipase beads comprise from 10 wt. % to 15 wt. % of pancrelipase based on a total weight of uncoated beads and from 80 wt. % to 85 wt. % of the at least one carrier based on the total weight of the uncoated beads.

9. The process of claim 4, wherein the enterically coated pancrelipase beads comprise 15 wt. % of pancrelipase based on a total weight of uncoated beads, 80 wt. % of the at least one carrier based on the total weight of the uncoated beads, and 5 wt. % of further excipients based on the total weight of the uncoated beads.

10. The process of claim 4, wherein the enterically coated pancrelipase beads comprise 10 wt. % of pancrelipase based on a total weight of uncoated beads, 85 wt. % of the at least one carrier based on the total weight of the uncoated beads, and 5 wt. % of further excipients, based on the total weight of the uncoated beads.

11. The process of claim 1, wherein the at least one carrier comprises the microcrystalline cellulose having a moisture content equal to or less than 5%, a nominal mean particle size of 160 µm, mesh size 38: amount retained: S 1.0%, mesh size 94: amount retained: S 50.0%, and mesh size 300: amount retained: S 70.0%.

12. The process of claim 1, wherein the at least one carrier comprises the microcrystalline cellulose having a moisture content equal to or less than 5%, a nominal mean particle size of 180 µm, mesh size 60: amount retained: S 10.0%, and mesh size 100: amount retained: S 50.0%.

13. The process of claim 1, wherein the at least one carrier comprises a first microcrystalline cellulose having a moisture content equal to or less than 5%, a nominal mean particle size of 160 µm, mesh size 38: amount retained: S 1.0%, mesh size 94: amount retained: S 50.0%, and mesh size 300: amount retained: S 70.0%, and a second microcrystalline cellulose having a moisture content equal to or less than 5%, a nominal mean particle size of 50 µm, mesh size 60: amount retained: S 1.0%, and mesh size 200: amount retained: S30.0%, and a weight ratio of the first and second microcrystalline cellulose is 16:1.

14. The process of claim 1, wherein the at least one carrier comprises a mixture of the microcrystalline cellulose and trehalose.

15. The process of claim 13, wherein the at least one carrier comprises the microcrystalline cellulose having a moisture content equal to or less than 5%, a nominal mean particle size of 160 µm, mesh size 38: amount retained: S 1.0%, a mesh size 94: amount retained: S 50.0%, and mesh size 300: amount retained: S 70.0% and trehalose, and a weight ratio of the microcrystalline cellulose and the trehalose is 1:1.

16. The process of claim 14, wherein the at least one carrier comprises the microcrystalline cellulose having a moisture content equal to or less than 5%, a nominal mean particle size of 180 µm, mesh size 60: amount retained: S 10.0%, mesh size 100; amount retained: S 50.0%, and trehalose, and a weight ratio of the microcrystalline cellulose and the trehalose is 1:1.

17. A process for the preparation of a dosage form comprising a pharmaceutical composition comprising a blend of at least one digestive enzyme and at least one carrier, the process comprising the following steps:
   a) mixing the at least one digestive enzyme and the at least one carrier, and optional further excipients;
   b) compressing the mixture into beads;
   c) optionally coating the beads with an enteric polymer; and
   d) preparing the dosage form with the optionally coated beads, wherein a total amount of the at least one digestive enzyme in the pharmaceutical composition is from 4% to 19% by weight, and the at least one carrier comprises microcrystalline cellulose having an average particle size greater than 100 μm.

18. The process of claim 17, wherein the dosage form is a capsule.

19. The process of claim 18, wherein the at least one digestive enzyme is lipase from 500 to 5,000 USP units.

20. The process of claim 19, wherein the at least one digestive enzyme is lipase from 675 to 825 USP units.

21. The process of claim 19, wherein the at least one digestive enzyme is lipase from 675 to 825 USP units, protease from 1,250 to 3,850 USP units, and amylase from 1,600 to 6,575 USP units.

22. The process of claim 17, wherein the dosage form is a capsule having a residual moisture content below 5%.

23. The process of claim 17, wherein the process further comprises step e) packaging the dosage form.

* * * * *